(12) United States Patent
Nakano et al.

(10) Patent No.: US 8,022,233 B2
(45) Date of Patent: Sep. 20, 2011

(54) PROCESS FOR PRODUCING GLYCIDYL 2-HYDROXYISOBUTYRATE AND COMPOSITION CONTAINING THE PRODUCT

(75) Inventors: Rieko Nakano, Niigata (JP); Masaki Takemoto, Niigata (JP); Yoshikazu Shima, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 667 days.

(21) Appl. No.: 11/993,999

(22) PCT Filed: Jun. 30, 2006

(86) PCT No.: PCT/JP2006/313081
§ 371 (c)(1),
(2), (4) Date: Dec. 27, 2007

(87) PCT Pub. No.: WO2007/004549
PCT Pub. Date: Jan. 11, 2007

(65) Prior Publication Data
US 2009/0030163 A1    Jan. 29, 2009

(30) Foreign Application Priority Data

Jul. 1, 2005   (JP) ................................. 2005-194149

(51) Int. Cl.
*C07D 301/12*   (2006.01)
*C08F 283/10*   (2006.01)
(52) U.S. Cl. ...................................... 549/531; 525/523
(58) Field of Classification Search .................. 525/523; 549/531
See application file for complete search history.

(56) References Cited

U.S. PATENT DOCUMENTS

| 5,106,458 | A | * | 4/1992 | Meyer et al. | 203/38 |
| 5,107,002 | A | * | 4/1992 | Shih | 549/542 |
| 6,849,162 | B2 | * | 2/2005 | Teles et al. | 203/38 |
| 7,074,946 | B2 | | 7/2006 | Shida et al. | |
| 2004/0249107 | A1 | * | 12/2004 | Muller et al. | 528/76 |
| 2005/0119496 | A1 | | 6/2005 | Shida et al. | |

FOREIGN PATENT DOCUMENTS

| CN | 1629127 A | 6/2005 |
| EP | 1538147 A1 | 6/2005 |
| JP | S61-183275 A1 | 8/1986 |
| JP | H01-42889 B | 9/1989 |
| JP | H08-188575 A | 7/1996 |
| JP | H09-100274 A | 4/1997 |
| JP | H09-301966 A | 11/1997 |
| JP | 2005-187453 A | 7/2005 |

OTHER PUBLICATIONS

Clerici et al., Synthesis of Propylene Oxide from Propylene and Hydrogen Peroxide Catalyzed by Titanium Silicalite, Journal of Catalysis, 129:159-167 (1991).*
Kraushaar et al., "New Method for the Preparation of Titanium-Silicalite (TS-1)," *Catalysis Letters* 1(4) 81 (1988), 81-84.
Reddy et al., "Titanium Silicalite-2: Synthesis Characterization," *Appl. Catal.*, 58(2), L1-L4 (1990).
Mario Clerici and Patrizia Ingallina; Epoxidation of Lower olefins with Hydrogen Peroxide and Titanium Silicalite; Journal of Catalysis; Sep. 4, 1992; 71-83; vol. 140; Academic Press, Inc.; San Donato Milanese, Milano, Italy.
Notification of First Office Action issued Jul. 30, 2010, in corresponding Chinese Application 200680023482.6.

* cited by examiner

*Primary Examiner* — Mark Eashoo
*Assistant Examiner* — Megan McCulley
(74) *Attorney, Agent, or Firm* — Fitch, Even, Tabin & Flannery

(57) ABSTRACT

An efficient process for producing glycidyl 2-hydroxyisobutyrate useful as a reactive diluent is provided. When glycidyl 2-hydroxyisobutyrate is produced by reacting allyl 2-hydroxyisobutyrate with hydrogen peroxide, a solution in which allyl 2-hydroxyisobutyrate is dissolved in an aliphatic ester as a solvent is reacted with hydrogen peroxide in the presence of a crystalline titanosilicate catalyst. Thus, a production process of glycidyl 2-hydroxyisobutyrate, which is small in degradation of purity and yield due to generation of peroxides or the like, and products thereof are provided.

7 Claims, No Drawings

PROCESS FOR PRODUCING GLYCIDYL 2-HYDROXYISOBUTYRATE AND COMPOSITION CONTAINING THE PRODUCT

This Application is the U.S. National Stage Application under 35 U.S.C. 371 of International Application PCT/JP2006/313081 filed Jun. 30, 2006, which designated the United States but was not published in English, and further claims the benefit from Japanese patent application number 2005-194149 filed Jul. 1, 2005, the complete disclosures of which are incorporated herein by reference.

TECHNICAL FIELD

The present invention relates to an efficient and industrially practicable process for obtaining glycidyl 2-hydroxyisobutyrate represented by the following formula (2) by epoxidizing allyl 2-hydroxyisobutyrate represented by the following formula (1) with hydrogen peroxide, and a reactive diluent and an epoxy resin composition containing the glycidyl 2-hydroxyisobutyrate obtained by the process.

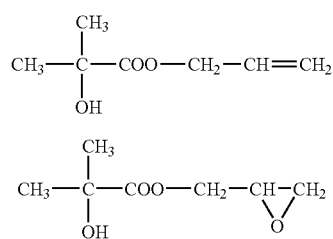

BACKGROUND ART

Processes that would be available for producing glycidyl carboxylates include (a) a process in which they are produced by a desalting condensation reaction of a carboxylic acid or a salt thereof with epichlorohydrin, and (b) a process in which the allyl group of an allyl ester is epoxidized. As for glycidyl 2-hydroxyisobutyrate having the structure represented by the formula (2), an example of the process (a) is known, in which glycidyl 2-hydroxyisobutyrate is produced from 2-hydroxyisobutyric acid and epichlorohydrin (see, for example, Patent Document 1), and an example of the process (b) is known, in which an allyl compound as an olefinically unsaturated compound is reacted with hydrogen peroxide to effect epoxidization in the presence of a crystalline titanosilicate catalyst using an alcohol, a ketone or an ether as a solvent (see, for example, Patent Documents 2 and 3). In the process (a), however, 2-hydroxyisobutyric acid as a reaction substrate is a compound containing a hydroxy group and a carboxyl group in one molecule, and hence causes side reactions at the time of the desalting condensation reaction with epichlorohydrin to give a reaction yield of 70% or less which is still unsatisfactory.

Additionally, an attempt to synthesize glycidyl 2-hydroxyisobutyrate having the structure represented by the above formula (2) was made by the present inventors in accordance with the process (b), and consequently no sufficient reaction rate was attained when the known solvent, namely, alcohol, ketone or ether was used, and little target compound was obtained when no solvent was used. On the other hand, although aliphatic esters typified by ethyl acetate lead to a lower risk of production of peroxides as compared to the above-described solvents (see, for example, Non-patent Document 1), aliphatic esters are poor in compatibility with hydrogen peroxide, water and the like, and there has been no report that an aliphatic ester is used in a reaction in which an olefinically unsaturated compound is reacted with hydrogen peroxide to effect epoxidization in the presence of a crystalline titanosilicate catalyst.

Patent Document 1: Japanese Patent Application No. 2004-338680
Patent Document 2: Japanese Patent Laid-Open No. 61-183275
Patent Document 3: Japanese Patent Laid-Open No. 08-188575
Non-patent Document 1: Kanagawa Industrial Technology Research Institute (Kanagawa-Ken Sangyo-Gijutu Sogo-Kenkyu-Sho); Heisei-15 (2003) Industry-Academia-Public Cooperation Conference Proceeding (San-Gaku-Ko Koryu Happyokai Siryo), p. 97.

DISCLOSURE OF THE INVENTION

Problems to be Solved by the Invention

If the compound represented by the above formula (2) which has plural characteristic reactive groups, can be easily and economically produced, the compound is expected to be used in various applications such as an application as a reactive diluent. In other words, an object of the present invention is to provide an industrially practicable process for producing, safely and with high yield, glycidyl 2-hydroxyisobutyrate which will be largely demanded as mentioned above.

Means for Solving the Problems

The present inventors have made a diligent investigation in order to solve the above-described problems, and have consequently made the present invention by discovering a process for producing, safely and with high yield, glycidyl 2-hydroxyisobutyrate in which a solution composed of allyl 2-hydroxyisobutyrate and an aliphatic ester as a solvent is reacted with hydrogen peroxide in a molar ratio of 0.2 or more and 1.0 or less relative to the 2-hydroxyisobutyric acid in a presence of a crystalline titanosilicate as a catalyst.

Specifically, the process of the present invention relates to the processes for efficiently producing glycidyl 2-hydroxyisobutyrate represented by the formula (2) by epoxidizing allyl 2-hydroxyisobutyrate under specific conditions, as defined the following (1) to (10).

(1) A process for producing glycidyl 2-hydroxyisobutyrate, characterized in that allyl 2-hydroxyisobutyrate is reacted with hydrogen peroxide in a presence of a crystalline titanosilicate as a catalyst and an aliphatic ester as a solvent.

(2) The process for producing glycidyl 2-hydroxyisobutyrate, according to the above item (1), wherein the crystalline titanosilicate as a catalyst is a pentasil-type titanosilicate.

(3) The process for producing glycidyl 2-hydroxyisobutyrate, according to the above item (1), wherein the aliphatic ester as a solvent is at least one selected from ethyl acetate, methyl formate and dimethyl carbonate.

(4) The process for producing glycidyl 2-hydroxyisobutyrate, according to the above item (1), wherein a hydrogen peroxide solution is used for the reaction with hydrogen peroxide.

(5) The process for producing glycidyl 2-hydroxyisobutyrate, according to the above items (1) to (4), wherein the molar ratio of hydrogen peroxide to be used for the reaction is 0.2 or more and 1.0 or less relative to allyl 2-hydroxyisobutyrate.

(6) The process for producing glycidyl 2-hydroxyisobutyrate, according to the above item (5), wherein the molar ratio of hydrogen peroxide to be used for the reaction is 0.3 or more and 0.7 or less relative to allyl 2-hydroxyisobutyrate.

(7) The process for producing glycidyl 2-hydroxyisobutyrate, according to the above items (1) to (6), wherein a predetermined amount of hydrogen peroxide is added to a suspension in which allyl 2-hydroxyisobutyrate, the crystalline titanosilicate as a catalyst and the aliphatic ester as a solvent are mixed.

(8) The process for producing glycidyl 2-hydroxyisobutyrate, according to the above items (1) to (6), wherein a solution comprising allyl 2-hydroxyisobutyrate and the aliphatic ester and a solution comprising hydrogen peroxide are introduced into a catalyst layer packed with the crystalline titanosilicate or a suspension comprising the crystalline titanosilicate.

(9) A reactive diluent for use in epoxy resin, which comprises the glycidyl 2-hydroxyisobutyrate obtained by the production process according to any one of the above items (1) to (8).

(10) An epoxy resin composition which comprises the reactive diluent for use in resin as defined in the above item (9).

EFFECTS OF THE INVENTION

By use of the method of the present invention, reaction efficiency is enhanced without impairing selectivity of glycidyl 2-hydroxyisobutyrate, and glycidyl 2-hydroxyisobutyrate can be easily and stably produced. The thus-obtained glycidyl 2-hydroxyisobutyrate is useful as a reactive diluent, and epoxy resin compositions containing the reactive diluent are suitably used for civil engineering/construction materials, embedding of electric/electronic components, casting, adhesion, coating, laminates and the like.

BEST MODE FOR CARRYING OUT THE INVENTION

The present invention uses, as a catalyst, a crystalline titanosilicate having a composition represented by a general formula, $xTiO_2 \cdot (1-x)SiO_2$ wherein $0.0001 < x < 0.5$, and more preferably $0.001 < x < 0.05$. Examples of the conventionally known processes for producing crystalline titanosilicates include a process in which a reaction mixture composed of a silicon source, a titanium source, a nitrogen-containing compound and water is prepared and subjected to hydrothermal synthesis to obtain a titanosilicate, and a process in which a zeolite such as ZSM-5 is dealuminated in the presence of hydrochloric acid to introduce Ti atoms into the zeolite (B. Kraushaar and J. H. C. Van Hoff, Catal. Lett., 1(4), 81, (1988)); any of these processes may be adopted, and herein, the former synthesis process is described in detail.

As the silicon source that can preferably be used, mention may be made of tetraalkylorthosilicate and colloidal silica. As tetraalkylorthosilicate, tetraethylorthosilicate is preferably used. As the Ti source, tetraalkylorthotitanates or hydrolyzable titanium halide compounds such as $TiOCl_2$ can be used. As tetraalkylorthotitanates, tetraethylorthotitanate and tetrabutylorthotitanate are preferably used.

As the nitrogen-containing compound, tetraalkylammonium ions, preferably tetrapropylammonium hydroxide and tetrabutylammoium hydroxide can be used. Additionally, amines that are generally used for preparing zeolite catalysts, such as choline, triethanolamine, diethanolamine and piperidine may be used as the nitrogen-containing compound, so that titanosilicates of various crystal forms can be synthesized.

In the present invention, crystalline titanosilicates are particularly preferably used, which have a crystal structure similar to that of ZMS-5 and are, in general, collectively called the pentasil-type. The molar ratios of the raw materials used in preparing the titanosilicate in the present invention are as follows: Si/Ti=10 to 50, $H_2O$/Si=10 to 100, and the nitrogen-containing compound/Si=0.05 to 1. Crystalline titanosilicate catalysts can be obtained by mixing the above-described raw materials, subjecting the resultant mixture to hydrothermal synthesis in an autoclave at 100 to 220° C. for 1 to 1000 hours, and washing the resultant solid with ion-exchanged water, followed by drying and subsequent calcination in air at 400 to 600° C. for 1 to 10 hours.

When tetrapropylammonium hydroxide is used as the nitrogen-containing compound, a titanosilicate (hereinafter, referred to as TS-1) having the silicalite-1 structure is obtained (Japanese Patent Publication (Kokoku) No. 1-42889), and when tetrabutylammonium hydroxide is used as the nitrogen-containing compound, a titanosllicate (hereinafter, referred to as TS-2) having a silicalite-2 structure is obtained (J. S. Reddy et al., Appl. Catal., 58(2), L1-L4, (1990)).

As the organic solvent used in the production process of the present invention, aliphatic esters are suitably used; among them, aliphatic esters having 1 to 5 carbon atoms are particularly preferable, and ethyl acetate, methyl formate and dimethyl carbonate are most preferable. There is an appropriate range of amount of the solvent to be used. When the solvent amount is too small, viscosity of the reaction solution is increased, thereby rendering removal of heat of reaction to be difficult, and causing side reactions such as production of a diol due to hydrolysis reaction of glycidyl 2-hydroxyisobutyrate disadvantageously. Additionally, if no solvent is used in the present invention, reaction rate is extremely decreased, and hence glycidyl 2-hydroxyisobutyrate as the target is hardly obtained. On the other hand, when the amount of the reaction solvent is too much, reaction rate is decreased, or concentration of the produced glycidyl 2-hydroxyisobutyrate in the reaction mixture is decreased, and hence the cost of energy required for separation and purification of the produced glycidyl 2-hydroxyisobutyrate becomes too high and uneconomical. Usually, the amount of the solvent is selected from a range of 5 to 90 wt % and more preferably from a range of 10 to 50 wt % relative to the total amount of the reaction mixture exclusive of the catalyst.

No particular constraint is imposed on the concentration of hydrogen peroxide used in the present invention; however, industrially available 30 to 60 wt % aqueous solutions of hydrogen peroxide are preferably used. When the molar ratio of hydrogen peroxide used in the reaction exceeds 1.0 relative to allyl 2-hydroxyisobutyrate, unreacted hydrogen peroxide causes side reactions with the produced glycidyl 2-hydroxyisobutyrate to degrade selectivity of the target product, and risk of explosion due to the unreacted hydrogen peroxide is increased disadvantageously. On the other hand, when the molar ratio of hydrogen peroxide is less than 0.2 relative to allyl 2-hydroxyisobutyrate, unreacted allyl 2-hydroxyisobutyrate remains in a large amount, and hence productivity is lowered, thereby incurring expenses for energy required for separation and recovery of the unreacted allyl 2-hydroxyisobutyrate from the reaction product. Accordingly, for the purpose of implementing the present invention, the amount of hydrogen peroxide to be used relative to allyl 2-hydroxyisobutyrate is preferably 0.2 or more and 1.0 or less, and more preferably 0.3 or more and 0.7 or less in terms of molar ratio.

Reaction temperature in the present reaction falls preferably in a range from 30 to 120° C., and more preferably in a range from 50 to 80° C. When the reaction temperature is lower than the above-described ranges, reaction rate is too slow to be practicable. When the reaction temperature is higher than the above-described ranges, proportion of side reactions is increased. The reaction producing glycidyl 2-hydroxyisobutyrate is an exothermic reaction, and hence the heat of reaction is preferably removed by means of an appropriate technique for the purpose of controlling the reaction temperature within a certain range.

As examples of reaction procedures in the present invention, mention may be made of various reaction procedures including a procedure in which a catalyst, a solvent and allyl 2-hydroxyisobutyrate are placed in a reactor such as a vessel-type stirred reactor and a solution containing hydrogen peroxide is added to the reactor to initiate the reaction, a procedure in which a catalyst and a solvent are placed in a reactor such as a vessel-type stirred reactor and a solution containing allyl 2-hydroxyisobutyrate and hydrogen peroxide is added to the reactor to initiate the reaction, and a procedure in which a catalyst is immobilized in a flow reactor, and a solvent, allyl 2-hydroxyisobutyrate and hydrogen peroxide are continuously introduced into the reactor to be allowed to react. The present invention may adopt any reaction procedure as long as the reaction procedure is capable of controlling the molar ratio of hydrogen peroxide so as not to exceed 1 relative to ally 2-hydroxyisobutyrate. On the other hand, a procedure in which a catalyst, a solvent and hydrogen peroxide are placed in a reactor such as a vessel-type stirred reactor, and allyl 2-hydroxyisobutyrate is added to the reactor to initiate the reaction is not preferable because this procedure causes side reactions to a normegligible extent.

From the resultant reaction solution, glycidyl 2-hydroxyisobutyrate with high purity can be obtained safely and with satisfactory yield by separating the reaction solvent, water, the unreacted allyl 2-hydroxyisobutyrate and the produced glycidyl 2-hydroxyisobutyrate by means of an operation such as reduced-pressure distillation.

The glycidyl 2-hydroxyisobutyrate obtained by the process of the present invention exhibits an excellent dilution effect when used as a reactive diluent for epoxy resin, and additionally is advantageous in that it does not lower the curing speed of the resin as compared to conventional reactive diluents. Additionally, epoxy resin compositions containing the present reactive diluent are suitably used for civil engineering/construction materials, embedding of electric/electronic components, casting, adhesion, coating, laminates and the like.

EXAMPLES

Hereinafter, the present invention will be described in more detail by way of Examples and Comparative Examples, but the present invention is not limited to these Examples.

Reference Examples

Preparation of Catalysts

TS-1 Catalyst

In a four-necked flask with a 500-ml internal volume, 106.6 g of tetraethylorthosilicate and 3.10 g of tetraethylorthotitanate were placed, and then, 195.1 g of a 19.1 wt % aqueous solution of tetrapropylammonium hydroxide was added thereto dropwise at a rate of 100 g/hr with an instillation pump under a nitrogen gas stream. During the dropwise addition, the temperature of the reaction solution was controlled within a range from 23 to 25° C. After completion of the dropwise addition, the reaction solution was continuously stirred for 17 hours until hydrolysis was completed, and thereafter the reaction solution was heated to 80° C. to distill off the ethanol produced by the hydrolysis from the reaction solution, to yield a transparent sol. The resulting sol was supplemented with 110 g of distilled water so that the weight of the entire solution became 262 g, and thereafter filled in a 500-ml SUS 316 autoclave.

After the gas in the autoclave was replaced with nitrogen, the autoclave was sealed and heated at 170° C. for two days, and thereafter heated to 210° C. and maintained at 210° C. for two further days, followed by being cooled to room temperature. The solution containing white solids was subjected to centrifugal separation for 20 minutes at 3000 rpm using a centrifugal separator, and separated into a nearly transparent supernatant liquid and white titanosilicate particles. The obtained white titanosilicate particles were washed with distilled water, and then dried at 80° C. for 6 hours. After sufficient drying, the white titanosilicate particles were subjected to calcination treatment in air at 550° C. for 6 hours in an electric furnace to yield 18.5 g of a crystalline titanosilicate (hereinafter, this catalyst is abbreviated as TS-1). The X-ray diffraction spectrum and the infrared absorption spectrum of the TS-1 were the same as the corresponding spectral charts presented in Patent Document 4

TS-2 Catalyst

In a four-necked flask with a 300-ml internal volume, 52.0 g of tetraethylorthosilicate and 1.47 g of tetraethylorthotitanate were placed, and then, 100.0 g of a 26 wt % aqueous solution of tetrabutylammonium hydroxide was added thereto dropwise at a rate of 80 g/hr with an instillation pump under a nitrogen gas stream. During the dropwise addition, the temperature of the reaction solution was controlled within a range from 23 to 25° C. After completion of the dropwise addition, the reaction solution was continuously stirred for 17 hours until hydrolysis was completed, and thereafter the reaction solution was heated to 70 to 80° C. to distill off the ethanol produced by the hydrolysis from the reaction solution, to yield a transparent sol. The resulting sol was supplemented with 25 g of distilled water so that the weight of the entire solution became 103 g, and thereafter filled in a 500-ml SUS 316 autoclave.

After the gas in the autoclave was replaced with nitrogen, the autoclave was sealed and heated at 170° C. for two days, and thereafter heated to 210° C. and maintained at 210° C. for two further days, followed by being cooled to room temperature. The solution containing white solids was subjected to centrifugal separation for 20 minutes at 3000 rpm using a centrifugal separator, and separated into a nearly transparent supernatant liquid and white titanosilicate particles. The obtained white titanosilicate particles were washed with distilled water, and then dried at 80° C. for 6 hours. After sufficient drying, the white titanosilicate particles were subjected to calcination treatment in air at 550° C. for 6 hours in an electric furnace to yield 13.6 g of a crystalline titanosilicate (hereinafter, this catalyst is abbreviated as TS-2). The X-ray diffraction spectrum and the infrared absorption spectrum of the TS-2 were the same as the corresponding spectral charts presented in Non-patent Document 3.

Example 1

In a 100-ml three-necked flask equipped with a magnetic stirrer, a thermometer and a reflux condenser, 20 g (0.139 mol) of allyl 2-hydroxyisobutyrate, 5.0 g (0.057 mol) of ethyl acetate and 1.0 g of the TS-1 catalyst prepared in the above-described catalyst preparation example were placed, and successively 5.25 g (0.093 mol, the raw material allyl 2-hydroxyisobutyrate:hydrogen peroxide=1.5:1 in molar ratio) of a 60 wt % hydrogen peroxide solution was added thereto dropwise at a reaction temperature of 70° C. over a period of 10 minutes. After completion of the dropwise addition, further the reaction solution was continuously stirred at 70° C. for 4 hours to complete the reaction. In the reaction solution from which the catalyst was filtered off after the completion of the reaction, the residual amount of allyl 2-hydroxyisobutyrate was 8.17 g (0.0567 mol) and the amount of the produced glycidyl 2-hydroxyisobutyrate was 11.90 g (0.0744 mol). The molar yield of glycidyl 2-hydroxyisobutyrate with reference to the amount of the added hydrogen peroxide was 80.3%, and the selectivity of glycidyl 2-hydroxyisobutyrate relative to the raw material allyl 2-hydroxyisobutyrate was 90.4%.

Comparative Example 1

In a 100-ml three-necked flask equipped with a magnetic stirrer, a thermometer and a reflux condenser, 20 g (0.139 mol) of allyl 2-hydroxyisobutyrate and 1.0 g of the TS-1 catalyst prepared in the above-described catalyst preparation example were placed, and successively 5.25 g (0.093 mol, the raw material allyl 2-hydroxyisobutyrate:hydrogen peroxide=1.5:1 in molar ratio) of a 60 wt % hydrogen peroxide solution was added thereto dropwise at a reaction temperature of 70° C. over a period of 10 minutes. After completion of the dropwise addition, further the reaction solution was continuously stirred at 70° C. for 4 hours to complete the reaction. In the reaction solution from which the catalyst was filtered off after the completion of the reaction, the residual amount of allyl 2-hydroxyisobutyrate was 18.69 g (0.130 mol) and the amount of the produced glycidyl 2-hydroxyisobutyrate was 0.16 g (0.001 mol). The molar yield of glycidyl 2-hydroxyisobutyrate with reference to the amount of the added hydrogen peroxide was 1.08%, and the selectivity of glycidyl 2-hydroxyisobutyrate relative to the raw material allyl 2-hydroxyisobutyrate was 10.9%.

Example 2

In a SUS 316 autoclave with a 20-ml internal volume, 2.04 g (0.014 mol) of allyl 2-hydroxyisobutyrate, 2.64 g (0.03 mol) of ethyl acetate, 0.51 g (0.009 mol) of a 60 wt % hydrogen peroxide solution and 0.2 g of the TS-1 catalyst prepared in the above-described catalyst preparation example were placed, and the contents of the autoclave was allowed to react with each other at 70° C. for 2 hours under stirring with the magnetic stirrer. In the reaction solution from which the catalyst was filtered off after the completion of the reaction, the residual amount of allyl 2-hydroxyisobutyrate was 0.92 g (0.0064 mol) and the amount of the produced glycidyl 2-hydroxyisobutyrate was 1.20 g (0.0075 mol). The molar yield of glycidyl 2-hydroxyisobutyrate with reference to the amount of the added hydrogen peroxide was 83.3%, and the selectivity of glycidyl 2-hydroxyisobutyrate relative to the raw material allyl 2-hydroxyisobutyrate was 96.4%. The results are shown in Table 1.

Example 3

In a SUS 316 autoclave with a 20-ml internal volume, 2.05 g (0.014 mol) of allyl 2-hydroxyisobutyrate, 2.64 g (0.03 mol) of ethyl acetate, 0.51 g (0.009 mol) of a 60 wt % hydrogen peroxide solution and 0.2 g of the TS-2 catalyst prepared in the above-described catalyst preparation example were placed, and the contents of the autoclave was allowed to react with each other at 70° C. for 2 hours under stirring with the magnetic stirrer. In the reaction solution from which the catalyst was filtered off after the completion of the reaction, the residual amount of allyl 2-hydroxyisobutyrate was 0.85 g (0.0059 mol) and the amount of the produced glycidyl 2-hydroxyisobutyrate was 1.21 g (0.0076 mol). The molar yield of glycidyl 2-hydroxyisobutyrate with reference to the amount of the added hydrogen peroxide was 84.2%, and the selectivity of glycidyl 2-hydroxyisobutyrate relative to the raw material allyl 2-hydroxyisobutyrate was 91.2%. The results are shown in Table 1.

Examples 4 and 5 and Comparative Examples 2 to 5

The reaction was carried out in the exactly same manner as in Example 2, except that the reaction solvent was changed. The results are shown in Table 1.

TABLE 1

| Example | Reaction solvent (remark) | Yield (%) | Selectivity (%) |
| --- | --- | --- | --- |
| Example 2 | Ethyl acetate | 83.3 | 96.4 |
| Example 3 | Ethyl acetate (TS-2 catalyst) | 84.2 | 91.2 |
| Example 4 | Methyl formate (reaction time: 1 hour) | 82.9 | 95.9 |
| Example 5 | Dimethyl carbonate | 83.0 | 91.8 |
| Comparative Example 2 | Methanol | 60.2 | 91.4 |
| Comparative Example 3 | Acetonitrile | 57.7 | 97.4 |
| Comparative Example 4 | Acetonitrile/methanol = 3 (weight ratio) | 69.1 | 97.1 |
| Comparative Example 5 | Dimethyl carbonate/methanol = 2 (weight ratio) | 60.1 | 93.8 |

Yield: With reference to hydrogen peroxide
Selectivity: Relative to allyl 2-hydroxyisobutyrate Example 6

(1) Catalyst Molding

To 98 parts by weight of the TS-1 catalyst prepared in the above-described catalyst preparation example, 2 parts by weight of carboxylmethyl cellulose ammonium was added, and the mixture was sufficiently blended in a Labomill, and thereafter processed into a paste by addition of an appropriate amount of water. The obtained paste was dried in an oven maintained at 150° C., and the resultant solid material was transferred into an alumina crucible to be calcined at 550° C. for 5 hours. The obtained solid material was crushed into 10 to 20 meshes and used for the reaction.

(2) Fixed Bed Flow-Through Reaction

In a glass reactor of 15 mmϕ in inner diameter and 600 mm in length equipped with a jacket, 42 g of the above-described molded catalyst was filled. Warm water at 65° C. was passed through the jacket. A raw material solution 1 prepared by mixing 40 parts by weight of allyl 2-hydroxyisobutyrate and 60 parts by weight of ethyl acetate and a 60 wt % hydrogen peroxide solution were simultaneously flowed through the reactor tube at 160 g/hr and 16.8 g/hr, respectively, to carry out the reaction. Due to exothermic reaction, a heated region appeared at the upper 3 to 5-cm portion of the catalyst layer. The peak temperature of the heated region was found to be 70 to 80° C. The solution collected at the exit of the reactor was analyzed. Relations of yield and selectivity with the elapsed time from the start of the reaction are shown in Table 2.

TABLE 2

| Elapsed reaction time (hr) | Yield (%) | Selectivity (%) |
|---|---|---|
| 52 | 82.3 | 88.4 |
| 123 | 77.3 | 91.7 |
| 225 | 76.4 | 93.5 |
| 302 | 77.9 | 93.6 |

Yield: With reference to hydrogen peroxide
Selectivity: Relative to allyl 2-hydroxyisobutyrate

The invention claimed is:

1. A process for producing glycidyl 2-hydroxyisobutyrate, which comprises reacting allyl 2-hydroxyisobutyrate with hydrogen peroxide in a presence of a crystalline titanosilicate as a catalyst, wherein a hydrogen peroxide solution is added to a solution containing allyl 2-hydroxyisobutyrate in an organic solvent that consists essentially of an aliphatic ester.

2. The process for producing glycidyl 2-hydroxyisobutyrate, according to claim 1, wherein the crystalline titanosilicate as a catalyst is a pentasil-type titanosilicate.

3. The process for producing glycidyl 2-hydroxyisobutyrate, according to claim 1, wherein the aliphatic ester as a solvent is at least one selected from ethyl acetate, methyl formate and dimethyl carbonate.

4. The process for producing glycidyl 2-hydroxyisobutyrate, according to claim 1, wherein the molar ratio of hydrogen peroxide to be used for the reaction is 0.2 or more and 1.0 or less relative to allyl 2-hydroxyisobutyrate.

5. The process for producing glycidyl 2-hydroxyisobutyrate, according to claim 4, wherein the molar ratio of hydrogen peroxide to be used for the reaction is 0.3 or more and 0.7 or less relative to allyl 2-hydroxyisobutyrate.

6. The process for producing glycidyl 2-hydroxyisobutyrate, according to claim 1, wherein a predetermined amount of hydrogen peroxide is added to a suspension in which allyl 2-hydroxyisobutyrate, the crystalline titanosilicate as a catalyst and the aliphatic ester as a solvent are mixed.

7. The process for producing glycidyl 2-hydroxyisobutyrate, according to claim 1, wherein a solution comprising allyl 2-hydroxyisobutyrate and the aliphatic ester and a solution comprising hydrogen peroxide are introduced into a catalyst layer packed with the crystalline titanosilicate or a suspension comprising the crystalline titanosilicate.

* * * * *